United States Patent [19]

Blackshear et al.

[11] 4,439,181

[45] Mar. 27, 1984

[54] POLYOL-HORMONE MIXTURE FOR USE IN CHRONIC PARENTERAL HORMONE ADMINISTRATION

[75] Inventors: Perry J. Blackshear, Cambridge; John L. Palmer, Watertown, both of Mass.; Thomas D. Rohde, Minneapolis, Minn.

[73] Assignee: Regents of the University of Minnesota, Minneapolis, Minn.

[21] Appl. No.: 228,097

[22] Filed: Jan. 26, 1981

[51] Int. Cl.$^3$ ............................................. A61M 5/00
[52] U.S. Cl. ................................................. 604/56
[58] Field of Search ............... 128/213 A, 213 R, 260, 128/214 R, 260, 214 F; 260/210; 604/27-28, 48-53, 56, 82-84, 92

[56] References Cited

U.S. PATENT DOCUMENTS 3,731,681  5/1973  Blackshear et al. .
4,306,553  12/1981  Dorman et al. ................ 128/213 R

OTHER PUBLICATIONS

Albisser et al: Diabetes 29: 241, 1980, pp. 241-243.

Lougheed et al: Diabetologia 19: 1, 1980, pp. 1-9.

*Primary Examiner*—C. Fred Rosenbaum
*Assistant Examiner*—T. J. Wallen
*Attorney, Agent, or Firm*—Burd, Bartz & Gutenkauf

[57] ABSTRACT

A method of preventing the precipitation of proteins, such as hormone preparations, within drug delivery systems that depend on the fluidity of the infusate for proper function. A polyol, such as glycerol, is mixed with the protein solution prior to the introduction of the solution into the drug delivery system. The polyol is added in amount sufficient to prevent precipitation of the protein during long-term storage in the drug delivery device. According to one form of usage, the protein-polyol solution is injected to the pressurized drug storage reservoir of an implanted infusion pump by injection through the patient's skin. As the solution is discharged from the delivery device by the constant pressure exerted upon the storage chamber, its low rate of flow is controlled by a restricted fluid passage. The solution is conveyed to an infusion site and diluted by the blood stream.

14 Claims, No Drawings

POLYOL-HORMONE MIXTURE FOR USE IN CHRONIC PARENTERAL HORMONE ADMINISTRATION

FIELD OF THE INVENTION

Background of the Invention

This invention relates to a method of preventing the precipitation of proteins, such as hormone preparations, within drug delivery systems that depend on the fluidity of the infusate for proper function. One system of this type is the implantable infusion pump illustrated and described in Blackshear et al U.S. Pat. No. 3,731,681, the disclosure of which is incorporated herein by reference. The addition of a polyol, such as glycerol, increases the solubility of the protein (i.e., a hormone, such as insulin) in water without affecting its biological activity. The polyol solubilizes both native or denatured proteins and inhibits the action of precipitation agents, such as adverse temperatures.

The control of many cellular functions in an organism is via hormones, such as insulin, human growth hormone, glucagon, and the like, secreted in very small amounts by specific glands into the blood stream. These hormones have high affinity for specific sites on or in the membranes of the specific cells. The hormones are typically small proteins with a marginal solubility in blood. The hormone is functionally active in the hydrophobic lipid membrane. A typical hormone deficiency disease is diabetes where the beta cells in the pancreas have been destroyed or are relatively ineffective, and the medical treatment is the administration of insulin.

Recent studies have suggested that management of blood glucose in diabetics can be improved by administering insulin by pump on a continuous basis, or in pulses several minutes apart, rather than by intermittent injections as is now common practice. One factor limiting the length of time this kind of administration can be maintained is precipitation of insulin in the flow passages of these pumps causing flow stoppage. There is mounting evidence that such improvement of control, if provided on a long-term basis, might inhibit or alleviate the development of diabetic complications such as blindness and kidney failure. Thus, the availability of an agent to maintain the solubility of insulin under those circumstances could potentially have substantial impact on the treatment of diabetes.

The magnitude of the problem of insulin precipitation in infusion device flow passages is summarized in the report of the National Conference on Diabetes held in Reston, Virginia on Oct. 9–12, 1979. There was a consensus of the Conference that:

"Almost all investigators agreed that a major (perhaps the major) impediment to long-term continuous insulin delivery is the aggregation of insulin into crystals and sludge which blocks tubing, membranes, and pump. System failure almost always eventually results. To date, no change in type or formulation of insulin nor change in system components has resolved this critical problem. New research into the physical-chemical properties of insulin is needed to solve this problem. The effort should be prompt and the support ample."

The implanted infusion pump of U.S. Pat. No. 3,731,681 has been used successfully to administer heparin for the treatment of blood clotting disorders. Heparin is a highly soluble and very negatively charged molecule. No difficulty was encountered with the metering of this drug using small bore capillary tubes or with the delivery of the drug to the blood stream using a conventional silicone rubber catheter. Over five years of continuous intravenous heparin delivery has been achieved in dogs with this system. Comparable infusion time periods were achieved when sterile water was substituted for heparin. However, when the same pump was used to deliver commercial regular insulin, in standard insulin diluting fluid, the pumps would flow normally for only one to two months. A progressive blockage of the passageways took place with eventual flow stoppage. Often a solid plug of amorphous proteinaceous material was found at the distal end of the small bore capillary, but plugs were found in some cases in the proximal end of the capillary or in the larger bore cannula. These plugs were dissimilar from thrombus plugs which sometimes occurred at the cannula tip.

Others using chronic insulin delivery systems have experienced similar problems. For review see Lougheed et al, Insulin Aggregation in Artificial Delivery Systems, Diabetologia 19:1, 1980. Long-term functioning of insulin delivery systems cannot be maintained using standard insulin preparations. The initial approach was to solve the problem of plugging by hardware changes. When these proved to be ineffective, the next approach was to alter the solution used to solubilize the insulin.

THE PRIOR ART

There is little prior art to draw from, since this invention deals with a device that has only recently been developed. We have found in previous experiments that a surfactant, sodium lauryl sulfate (as described in copending Dorman et al U.S. Patent Application Ser. No. 171,091 now U.S. Pat. No. 4,306,553) will prevent the precipitation of insulin in the pump's delivery cannula. However, this compound has not yet been proven safe when used intravenously in man. Another possible solution was recently described using a different pump by Albisser and colleagues (Albisser, A. M., et al: Diabetes 29:241, 1980). In their portable peristaltic pump, the addition of 1.5% autologous serum prevented the precipitation and loss of insulin potency that occurred without serum. However, use of 1.5% serum in our animal studies failed to prevent clogging of the capillary tubes with insulin, possibly because the major differences in inner diameter between our capillary tubing and Albisser's delivery cannula. Lougheed et al (Insulin Aggregation in Artificial Delivery Systems, Diabetologia 19:1, 1980) tested the ability of glycerol at 1.27 g/100 ml to prevent insulin aggregation when subjected to vigorous shaking and found that it was not successful. It is likely that the concentration of glycerol was too low to have the desired effect. Thus, the prior art to our knowledge, consists of one compound, sodium lauryl sulfate, that is effective but of unproven nontoxicity, and autologous serum, which is not effective in our device.

SUMMARY OF THE INVENTION

Broadly stated, this invention is directed to a method of maintaining the fluidity of protein solutions for parenteral administration at a low flow rate to a chronically ill patient suffering from a protein-deficiency disease from an implanted pressure actuated drug delivery device without loss of biological activity. A polyol, such as glycerol, is mixed with the protein solution prior to the injection of the solution into the drug storage chamber of the delivery device, for thorough dissolution and uniform distribution through the solution. The polyol is added in an amount sufficient to prevent precipitation of the protein during long-term storage in the drug delivery device of up to several weeks. Thereafter, the protein-polyol solution is injected into the drug storage chamber by injection through the patient's skin. As the solution is discharged from the delivery device by the constant pressure exerted upon the storage chamber, its low rate of flow is controlled by a restricted fluid passage. The solution is conveyed to an infusion site by tubular passage means, such as a small diameter catheter.

DETAILED DESCRIPTION OF THE PREFERRED EMBODIMENT

According to the invention, a polyol solution, such as a solution of glycerol, is admixed with a solution of protein, such as a standard injectable hormone solution, so that the final concentration of polyol in the solution is from about 10 to 90% by volume, and preferably about 50 to 80%, sufficient to prevent precipitation of the protein after charging into the drug storage chamber of a pressure actuated drug delivery device, such as the infusion pump of U.S. Pat. No. 3,731,681.

The protein-polyol solution is injected into the drug storage chamber of the drug delivery device of a patient suffering from a protein-deficiency disease. From the storage chamber the solution is discharged through a fluid restrictor at a low flow rate of from about 1 cc to 15 cc per day, depending upon the needs of the patient, and passed into the blood stream at the desired infusion site. Upon passage into the blood stream, the solution is immediately diluted to below about 0.15% by weight to rapidly return the protein to its normal state where it may function normally with no loss of activity.

When given orally or intravenously in man in pharmacologic amounts, glycerol appears to be non-toxic. It is a low molecular weight organic compound of the structure: $CH_2OHCHOHCH_2OH$ that is a normal component of human and animal tissues and plasma. It is formed by the breakdown of triglycerides in human fat, and released into the blood in large amounts, where it can be easily measured. It is taken up by the liver from the blood and used in the formation there of glucose and fats. As a normal product of human metabolism, glycerol is released into the blood in amounts of about 20 grams per day for an average person.

In addition to being a normal component of human tissues and blood, glycerol has been used pharmacologically for many years. Given orally in high doses (100–200 g/day), it has a mild cathartic effect, and has been therapeutically useful in preventing brain swelling due to brain tumors (Bedikian, A. Y. et al, Cancer Treat. Rep. 62:1081, 1978). These authors gave 33 patients 100–140 g of glycerol per day, and noted no adverse effects save for occasional nausea and vomiting (also symptoms of the patients' underlying disease). Many other investigators have given glycerol intravenously to reduce brain swelling in stroke. In this situation, it is generally given in doses of 50 g/day, in 10% solutions; at such doses, no side effects are noted (Mathew, N. T. et al, Lancet 2:1327, 1972; Meyer, J. J. et al, Stroke 3:168, 1972; Sloviter, H. A., J. Clin. Invest. 37:619, 1958). It has been noted that when high doses of very high concentrations (above 50%) are used, mild hemolysis can result; this is prevented by use of 10% solutions or less rapid administration (Sloviter, supra; Tourtellotte, W. W. et al, Clin. Pharmacol. Ther. 13:159, 1972).

Glycerol is known as a natural protector of enzymes and other proteins against denaturation as from temperature and pH changes as well as other challenges. Glycerol stabilizes enzymes against cold inactivation in every situation in which this has been examined. It also protects many enzymes against denaturation by heat, and is used as a cryoprotectant in the freezing of blood cells, sperm, and other tissues. In most cases, concentrations of about 50% appear optimum for these applications.

The invention is illustration by the following examples:

EXAMPLE 1

The efficacy of glycerol in maintaining the solubility of insulin in an implanted infusion pump was tested. Implantable infusion pumps according to U.S. Pat. No. 3,731,681 were implanted in dogs according to the standard technique described by Blackshear et al, One Year of Continuous Heparinization in the Dog Using a Totally Implantable Infusion Pump, Surgery, Gynecology and Obstetrics, Vol. 141, pp. 176–186 (1975). Each pump was placed subcutaneously in the groin of the dog with its delivery cannula threaded into its inferior vena cava, the large vein draining the lower extremities. An insulin glycerol solution containing 80 percent by volume of glycerol was injected into each pump through the skin as needed to maintain a supply of insulin in the drug storage chamber of the implanted pump. To date, delivery tubing of pumps infusing insulin protected by 80 percent glycerol have remained patent from 266 to 296 days. This compares with infusion times of 18 to 43 days in pumps with unprotected insulin. The mean time for nine pumps with unprotected insulin was 33.8 days.

EXAMPLE 2

In a clinical test, an implantable infusion pump charged with insulin protected by 70 percent glycerol has functioned to date for more than two months with no evidence of slow-down. Since the flow rates from pumps with unprotected insulin drop off rapidly, the lack of evidence of slow-down after more than two months is indicative of a much longer running time without plugging.

EXAMPLE 3

In another animal experiment, an infusion pump implanted in a dog was filled with insulin protected by 50 percent glycerol. This pump operated for 100 days before plugging, compared with 18 to 43 days when unprotected insulin is used.

Although the invention has been described with particular reference to the use of glycerol, other biocompatible C-4 to C-18 polyols, including sugars, behave similarly to glycerol as protectors of protein structure and function. Exemplary of such other polyols are C-4: erythritol; C-5: arabinose, xylose, ribose, adonitol (ribitol) and arabitol; C-6: rhamose, inositol, fructose, galactose, glucose, mannose and sorbose; C-12: maltose and sucrose; and C-18: melezitose and raffinose. Where solid polyols are used they are dissolved in the standard aqueous insulin solution, or first prepared as an aqueous solution and admixed with the insulin, to provide a final concentration of polyol in the solution of about 10 to 90% weight/volume, and preferably about 50 to 80%. Similarly, although the invention is described with particular reference to solubilization of insulin, other infusible proteins are subject to the same precipitation problems, including growth hormone, glucagon, and the like.

It is apparent that many modifications and variations of this invention as hereinbefore set forth may be made without departing from the spirit and scope thereof. The specific embodiments described are given by way of example only and the invention is limited only by the terms of the appended claims.

The embodiments of the invention in which an exclusive property or privilege is claimed are defined as follows:

1. A method of maintaining the fluidity of protein solutions for parenteral administration at a low flow rate to a chronically ill patient suffering from a protein-deficiency disease from a drug delivery device that depends on the fluidity of the infusate for proper functioning, without loss of biological activity, which method comprises:
    (A) dissolving an effective amount between about 10 and 90 percent by weight/volume, sufficient to prevent precipitation of the protein, of a biocompatible C-4 to C-18 polyol in the protein solution prior to injection into the drug storage chamber of the delivery device, and
    (B) charging the drug storage chamber of the drug delivery device with said protein-polyol solution.

2. A method according to claim 1 wherein said protein is a hormone.

3. A method according to claim 2 wherein said hormone is insulin.

4. A method according to claim 1 wherein said drug delivery device is an implanted pressure actuated device whose storage chamber is charged by injection of the protein-polyol solution through the skin of the patient.

5. A method according to claim 1 wherein said polyol is glycerol present in amount between about 10 and 90 percent by volume.

6. A method according to claim 5 wherein said glycerol is present in amount between about 50 and 80 percent by volume.

7. A method according to claim 1 wherein said polyol is a solid selected from the class consisting of ribose, xylose, mannose, fructose and sorbose present in amount between about 10 and 90 percent by weight.

8. A method of administering a protein solution at a low flow rate to a chronically ill patient suffering from a protein-deficiency disease, which method comprises:
    (A) dissolving an effective amount between about 10 and 90 percent by weight/volume, sufficient to prevent precipitation of the protein, of a biocompatible C-4 to C-18 polyol in the protein solution to maintain the fluidity of the solution without loss of biological activity,
    (B) charging the drug storage chamber of a drug delivery device that depends on the fluidity of the infusate for proper functioning with the protein-polyol solution,
    (C) continuously discharging the solution from the storage chamber through a restricted flow passage into the blood stream of the patient at a rate between about 1 cc and 15 cc solution per day, and
    (D) diluting the solution with the blood stream as it enters the blood stream.

9. A method according to claim 2 wherein said protein is a hormone.

10. A method according to claim 9 wherein said hormone is insulin.

11. A method according to claim 2 wherein said drug delivery device is an implanted pressure actuated device whose storage chamber is charged by injection of the protein-polyol solution through the skin of the patient.

12. A method according to claim 8 wherein said polyol is glycerol present in amount between about 10 and 90 percent by volume.

13. A method according to claim 16 wherein said glycerol is present in amount between about 50 and 80 percent by volume.

14. A method according to claim 8 wherein said polyol is a solid selected from the class consisting of ribose, xylose, mannose, fructose and sorbose present in amount between about 10 and 90 percent by weight.

* * * * *

UNITED STATES PATENT AND TRADEMARK OFFICE
CERTIFICATE OF CORRECTION

PATENT NO. : 4,439,181

DATED : March 27, 1984

INVENTOR(S) : Perry J. Blackshear et al

It is certified that error appears in the above-identified patent and that said Letters Patent are hereby corrected as shown below:

Column 2, line 46, "the" should be --of--.

Column 6, claim 13, "claim 16" should be --claim 12--.

Signed and Sealed this

Eleventh Day of September 1984

[SEAL]

Attest:

GERALD J. MOSSINGHOFF

*Attesting Officer*  *Commissioner of Patents and Trademarks*